(12) United States Patent
Sowards et al.

(10) Patent No.: US 12,246,139 B2
(45) Date of Patent: Mar. 11, 2025

(54) CATHETER WITH OPTIC SHAPE SENSING CAPABILITIES

(71) Applicant: Bard Access Systems, Inc., Salt Lake City, UT (US)

(72) Inventors: Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 340 days.

(21) Appl. No.: 17/187,536

(22) Filed: Feb. 26, 2021

(65) Prior Publication Data

US 2021/0268229 A1   Sep. 2, 2021

Related U.S. Application Data

(60) Provisional application No. 62/983,396, filed on Feb. 28, 2020.

(51) Int. Cl.
*A61M 25/00* (2006.01)

(52) U.S. Cl.
CPC . *A61M 25/0026* (2013.01); *A61M 2025/0042* (2013.01); *A61M 2205/3327* (2013.01); *A61M 2205/587* (2013.01)

(58) Field of Classification Search
CPC ............ A61M 25/0026; A61M 25/005; A61M 25/0043; A61M 25/00; A61M 25/0021; A61M 25/0082; A61M 25/0105; A61M 25/0023; A61M 2025/0042; A61M 2025/0037; A61M 2025/0166; A61M 2205/3327; A61M 2205/587; A61B 5/065;
(Continued)

(56) References Cited

U.S. PATENT DOCUMENTS

| 3,493,288 A | 2/1970 | Oltman et al. |
| 4,768,855 A | 9/1988 | Nishi et al. |
| 4,813,429 A | 3/1989 | Eshel et al. |

(Continued)

FOREIGN PATENT DOCUMENTS

| CA | 3025240 A1 | 11/2017 |
| DE | 102016109601 A1 | 11/2017 |

(Continued)

OTHER PUBLICATIONS

PCT/US2021/054802 filed Oct. 13, 2021 International Search Report and Written Opinion dated Feb. 2, 2022.
(Continued)

*Primary Examiner* — Laura A Bouchelle
*Assistant Examiner* — Sarah Dympna Grasmeder
(74) *Attorney, Agent, or Firm* — Rutan & Tucker LLP

(57) ABSTRACT

A catheter with optic shape sensing capabilities is described. The catheter features an elongated tubing, one or more septums and one or more micro-lumens formed in an axial wall of the tubing and/or the one or more septums. A single core optical fiber can be configured to reside within each of the micro-lumens, the optical fibers in the plurality of lumens being spatially distributed to sense strain and return light signals with characteristics that identify the sensed strain for three-dimensional rendering of the catheter by a console during insertion into a body of a patient.

26 Claims, 8 Drawing Sheets

(58) Field of Classification Search
CPC ............ A61B 34/20; A61B 2034/2046; A61B 2034/2061; A61B 2034/2072
See application file for complete search history.

(56) References Cited

U.S. PATENT DOCUMENTS

| | | |
|---|---|---|
| 5,099,845 A | 3/1992 | Besz et al. |
| 5,163,935 A | 11/1992 | Black et al. |
| 5,178,153 A | 1/1993 | Einzig |
| 5,207,672 A | 5/1993 | Roth et al. |
| 5,211,165 A | 5/1993 | Dumoulin et al. |
| 5,220,703 A | 6/1993 | Kanayama et al. |
| 5,275,151 A | 1/1994 | Shockey et al. |
| 5,295,212 A | 3/1994 | Morton et al. |
| 5,423,321 A | 6/1995 | Fontenot |
| 5,454,807 A | 10/1995 | Lennox et al. |
| 5,517,997 A | 5/1996 | Fontenot |
| 5,599,492 A | 2/1997 | Engelson |
| 5,622,170 A | 4/1997 | Schulz |
| 5,633,494 A | 5/1997 | Danisch |
| 5,693,043 A | 12/1997 | Kittrell et al. |
| 5,740,808 A | 4/1998 | Panescu et al. |
| 5,827,313 A | 10/1998 | Ream |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 5,957,831 A | 9/1999 | Adair |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,210,362 B1 | 4/2001 | Ponzi |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,619,857 B2 | 9/2003 | Miyake |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 6,975,803 B2 | 12/2005 | Koide et al. |
| 7,132,645 B2 | 11/2006 | Kom |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,699,855 B2 | 4/2010 | Anderson et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,197,494 B2 | 6/2012 | Jaggi et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,119,551 B2 | 9/2015 | Qi et al. |
| 9,186,046 B2 * | 11/2015 | Ramamurthy ....... A61B 1/0017 |
| 9,339,206 B2 | 5/2016 | Grunwald |
| 9,345,510 B2 | 5/2016 | Patel et al. |
| 9,360,630 B2 | 6/2016 | Jenner et al. |
| 9,549,685 B2 | 1/2017 | Cox et al. |
| 9,560,954 B2 | 2/2017 | Jacobs et al. |
| 9,572,492 B2 | 2/2017 | Simpson et al. |
| 9,622,706 B2 | 4/2017 | Dick et al. |
| 9,645,326 B1 | 5/2017 | Sausse et al. |
| 9,649,048 B2 | 5/2017 | Cox et al. |
| 9,678,275 B1 | 6/2017 | Griffin |
| 9,678,284 B2 | 6/2017 | Coggi et al. |
| 9,872,978 B1 | 1/2018 | Zaborsky et al. |
| 10,231,643 B2 | 3/2019 | Grunwald |
| 10,231,753 B2 | 3/2019 | Burnside et al. |
| 10,258,240 B1 | 4/2019 | Eberle et al. |
| 10,265,133 B1 | 4/2019 | McClellan |
| 10,327,830 B2 | 6/2019 | Grant et al. |
| 10,349,890 B2 | 7/2019 | Misener et al. |
| 10,448,837 B2 | 10/2019 | Manzke et al. |
| 10,492,876 B2 | 12/2019 | Anastassiou et al. |
| 10,568,586 B2 | 2/2020 | Begin et al. |
| 10,603,126 B2 | 3/2020 | Karguth et al. |
| 10,620,386 B2 | 4/2020 | Van Der Mark et al. |
| 10,631,718 B2 | 4/2020 | Petroff et al. |
| 10,932,670 B2 | 3/2021 | Smith et al. |
| 10,939,889 B2 | 3/2021 | Flexman et al. |
| 10,992,078 B2 | 4/2021 | Thompson et al. |
| 10,992,079 B2 | 4/2021 | Stats et al. |
| 11,000,207 B2 | 5/2021 | Burnside et al. |
| 11,000,265 B1 | 5/2021 | Ryu et al. |
| 11,103,321 B2 | 8/2021 | Braun et al. |
| 11,123,047 B2 | 9/2021 | Jaffer et al. |
| 11,259,892 B2 | 3/2022 | Hufford et al. |
| 11,284,916 B2 | 3/2022 | Patel et al. |
| 11,382,653 B2 | 7/2022 | Patel et al. |
| 11,474,310 B2 | 10/2022 | Sowards et al. |
| 11,525,670 B2 | 12/2022 | Messerly et al. |
| 11,547,282 B2 | 1/2023 | Weise et al. |
| 11,607,150 B2 | 3/2023 | Schweikert et al. |
| 11,621,518 B2 | 4/2023 | Stats et al. |
| 11,707,205 B2 | 7/2023 | Messerly et al. |
| 11,806,096 B2 | 11/2023 | Flatt et al. |
| 11,850,073 B2 | 12/2023 | Wright et al. |
| 11,931,112 B2 | 3/2024 | Thompson et al. |
| 2002/0019627 A1 | 2/2002 | Maguire et al. |
| 2002/0087206 A1 | 7/2002 | Hirschberg et al. |
| 2002/0166190 A1 | 11/2002 | Miyake et al. |
| 2002/0188285 A1 | 12/2002 | Brown |
| 2002/0198457 A1 | 12/2002 | Tearney et al. |
| 2003/0045798 A1 | 3/2003 | Hular et al. |
| 2003/0092995 A1 | 5/2003 | Thompson |
| 2004/0111020 A1 | 6/2004 | Long |
| 2004/0111147 A1 | 6/2004 | Rabkin et al. |
| 2004/0242995 A1 | 12/2004 | Maschke |
| 2004/0260182 A1 | 12/2004 | Zuluaga et al. |
| 2005/0033264 A1 | 2/2005 | Redinger |
| 2006/0013523 A1 | 1/2006 | Childers et al. |
| 2006/0036164 A1 | 2/2006 | Wilson et al. |
| 2006/0100610 A1 | 5/2006 | Wallace et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0060847 A1 | 3/2007 | Leo et al. |
| 2007/0156019 A1 | 7/2007 | Larkin et al. |
| 2007/0179485 A1 | 8/2007 | Yeik et al. |
| 2007/0201793 A1 | 8/2007 | Askins et al. |

(56) References Cited

U.S. PATENT DOCUMENTS

| | | |
|---|---|---|
| 2007/0253673 A1 | 11/2007 | Nielsen et al. |
| 2007/0287886 A1 | 12/2007 | Saadat |
| 2007/0299425 A1 | 12/2007 | Waner et al. |
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1 | 11/2008 | Peh et al. |
| 2008/0285909 A1 | 11/2008 | Younge et al. |
| 2009/0005675 A1 | 1/2009 | Grunwald et al. |
| 2009/0018393 A1 | 1/2009 | Dick et al. |
| 2009/0046980 A1 | 2/2009 | Rohlen |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1 | 10/2009 | Gill et al. |
| 2009/0304582 A1 | 12/2009 | Rousso et al. |
| 2009/0318757 A1* | 12/2009 | Singh ................ A61B 1/012 600/109 |
| 2009/0324161 A1 | 12/2009 | Prisco |
| 2010/0016729 A1 | 1/2010 | Futrell |
| 2010/0030063 A1 | 2/2010 | Lee et al. |
| 2010/0063534 A1 | 3/2010 | Kugler et al. |
| 2010/0114115 A1 | 5/2010 | Schlesinger et al. |
| 2010/0114190 A1 | 5/2010 | Bendett et al. |
| 2010/0139669 A1 | 6/2010 | Piferi et al. |
| 2010/0204569 A1 | 8/2010 | Burnside et al. |
| 2010/0286531 A1 | 11/2010 | Ryan et al. |
| 2010/0292758 A1 | 11/2010 | Lee et al. |
| 2011/0087112 A1 | 4/2011 | Leo et al. |
| 2011/0098533 A1 | 4/2011 | Onoda et al. |
| 2011/0144481 A1 | 6/2011 | Feer et al. |
| 2011/0144630 A1 | 6/2011 | Loeb |
| 2011/0166442 A1 | 7/2011 | Sarvazyan |
| 2011/0172680 A1 | 7/2011 | Younge et al. |
| 2011/0178509 A1 | 7/2011 | Zerfas et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1 | 6/2013 | Manzke et al. |
| 2013/0188855 A1 | 7/2013 | Desjardins et al. |
| 2013/0190741 A1 | 7/2013 | Moll et al. |
| 2013/0204124 A1 | 8/2013 | Duindam et al. |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0031674 A1 | 1/2014 | Newman et al. |
| 2014/0046261 A1 | 2/2014 | Newman et al. |
| 2014/0058368 A1 | 2/2014 | Hogue |
| 2014/0088413 A1 | 3/2014 | Von Bucsh et al. |
| 2014/0121468 A1 | 5/2014 | Eichenholz |
| 2014/0155948 A1 | 6/2014 | Walsh et al. |
| 2014/0188133 A1 | 7/2014 | Misener |
| 2014/0221829 A1 | 8/2014 | Maitland et al. |
| 2014/0259477 A1 | 9/2014 | Huang |
| 2014/0275997 A1 | 9/2014 | Chopra et al. |
| 2014/0318825 A1 | 10/2014 | Erb et al. |
| 2014/0378945 A1 | 12/2014 | Beri |
| 2015/0029511 A1 | 1/2015 | Hooft et al. |
| 2015/0031987 A1 | 1/2015 | Pameijer et al. |
| 2015/0045649 A1 | 2/2015 | O'Dea et al. |
| 2015/0080688 A1 | 3/2015 | Cinbis et al. |
| 2015/0099979 A1 | 4/2015 | Caves et al. |
| 2015/0105654 A1 | 4/2015 | Meyer |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0244465 A1 | 8/2015 | Chou et al. |
| 2015/0270900 A1 | 9/2015 | Hilario et al. |
| 2015/0301288 A1 | 10/2015 | Thornton, Jr. |
| 2015/0305816 A1 | 10/2015 | Hadzic |
| 2015/0320977 A1 | 11/2015 | Vitullo et al. |
| 2016/0018602 A1 | 1/2016 | Govari et al. |
| 2016/0151115 A1 | 6/2016 | Karguth et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1* | 7/2017 | Liu ................ A61B 5/6852 |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0303824 A1 | 10/2017 | Schlesinger et al. |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2018/0369432 A1* | 12/2018 | Zaborsky .......... A61M 25/0097 |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | QI et al. |
| 2019/0374196 A1 | 12/2019 | Courtney et al. |
| 2020/0046434 A1 | 2/2020 | Graetzel et al. |
| 2020/0155073 A1 | 5/2020 | Hwang et al. |
| 2020/0170724 A1 | 6/2020 | Flatt et al. |
| 2020/0188036 A1 | 6/2020 | Ding et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1 | 2/2021 | Thompson et al. |
| 2021/0298680 A1 | 3/2021 | Sowards et al. |
| 2021/0154440 A1 | 5/2021 | Misener |
| 2021/0156676 A1 | 5/2021 | Messerly et al. |
| 2021/0205585 A1* | 7/2021 | Ullmann .......... A61M 25/0023 |
| 2021/0215871 A1 | 7/2021 | Hayes et al. |
| 2021/0271035 A1 | 9/2021 | Sowards et al. |

(56) References Cited

U.S. PATENT DOCUMENTS

| | | |
|---|---|---|
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Visener et al. |
| 2022/0110695 A1 | 4/2022 | Sowards et al. |
| 2022/0110706 A1 | 4/2022 | Misener et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2023/0082991 A1 | 3/2023 | Sowards et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 3545849 A1 | 10/2019 |
| EP | 3725252 A1 | 10/2020 |
| WO | 99/64099 A1 | 12/1999 |
| WO | 1999064099 A1 | 12/1999 |
| WO | 2006080076 A1 | 8/2006 |
| WO | 2006122001 A2 | 11/2006 |
| WO | 2009/155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016/061431 A1 | 4/2016 |
| WO | 2016193051 A1 | 12/2016 |
| WO | 2018071490 A1 | 4/2018 |
| WO | 2018/096491 A1 | 5/2018 |
| WO | 2019037071 A1 | 2/2019 |
| WO | 2019/046769 A1 | 3/2019 |
| WO | 2019230713 A1 | 12/2019 |
| WO | 2020/142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022/031613 A1 | 2/2022 |
| WO | 2022/081586 A1 | 4/2022 |
| WO | 2022/081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

PCT/US2021/060849 filed Nov. 24, 2021 International Search Report and Written Opinion dated Mar. 9, 2022.

U.S. Appl. No. 15/947,267, filed Apr. 6, 2018 Final Office Action dated Apr. 22, 2022.

PCT/US2018/026493 filed Apr. 6, 2018 International Search Report and Written Opinion dated Jun. 22, 2018.

PCT/US2020/044801 filed Aug. 3, 2020 International Search Report and Written Opinion dated Oct. 26, 2020.

U.S. Appl. No. 15/947,267, filed Apr. 6, 2018 Final Office Action dated Nov. 10, 2020.

U.S. Appl. No. 15/947,267, filed Apr. 6, 2018 Non-Final Office Action dated Mar. 12, 2021.

U.S. Appl. No. 15/947,267, filed Apr. 6, 2018 Non-Final Office Action dated May 29, 2020.

PCT/US2021/054596 filed Oct. 12, 2021 International Search Report and Written Opinion dated Jan. 26, 2022.

PCT/US2022/043698 filed Sep. 15, 2022 International Search Report and Written Opinion dated Dec. 19. 2022.

U.S. Appl. No. 17/967,794, filed Oct. 17, 2022 Notice of Allowance dated Feb. 15, 2023.

PCT/US2021/038899 filed Jun. 24, 2021 International Search Report and Written Opinion dated Oct. 6, 2021.

PCT/US2021/038954 filed Jun. 24, 2021 International Search Report and Written Opinion dated Oct. 28, 2021.

PCT/US2021/041128 filed Jul. 9, 2021 International Search Report and Written Opinion dated Oct. 25, 2021.

PCT/US2021/044216 filed Aug. 2, 2021 International Search Report and Written Opinion dated Nov. 18, 2021.

U.S. Appl. No. 17/185,777, filed Feb. 25, 2021 Non-Final Office Action dated Feb. 9, 2022.

PCT/US2020/062396 filed Nov. 25, 2020 International Search Report and Written Opinion dated Mar. 2, 2021.

PCT/US2020/062407 filed Nov. 25, 2020 International Search Report and Written Opinion dated Mar. 11, 2021.

PCT/US2021/020732 filed Mar. 3, 2021 International Search Report and Written Opinion dated Jul. 5, 2021.

U.S. Appl. No. 15/947,267, filed Apr. 6, 2018 Non-Final Office Action dated Oct. 13, 2021.

PCT/US2021 /059755 filed Nov. 17, 2021 International Search Report and Written Opinion dated Apr. 29, 2022.

PCT/US2021/024969 filed Mar. 30, 2021 International Search Report and Written Opinion dated Jul. 19, 2021.

U.S. Appl. No. 17/185,777, filed Feb. 25, 2021 Notice of Allowance dated Jun. 10, 2022.

PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.

U.S. Appl. No. 15/947,267, filed Apr. 6, 2018 Final Office Action dated Jun. 30, 2021.

PCT/US2023/014849 filed Mar. 8, 2023 International Search Report and Written Opinion dated Jun. 7, 2023.

PCT/US2023/015416 filed Mar. 16, 2023 International Search Report and Written Opinion dated May 26, 2023.

PCT/US2023/015536 filed Mar. 17, 2023 International Search Report and Written Opinion dated Jun. 22, 2023.

U.S. Appl. No. 17/217,852, filed Mar. 30, 2021 Non Final Office Action dated Jun. 7, 2023.

U.S. Appl. No. 17/217,852, filed Mar. 30, 2021 Restriction Requirement dated Mar. 21, 2023.

(56) References Cited

OTHER PUBLICATIONS

U.S. Appl. No. 17/499,644, filed Oct. 12, 2021 Restriction Requirement dated Jul. 11, 2023.
U.S. Appl. No. 17/697,895, filed Mar. 17, 2022 Non Final Office Action dated Jun. 14, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020042 filed Apr. 26, 2023 International Search Report and Written Opinion dated Sep. 26, 2023.
PCT/US2023/020044 filed Apr. 26, 2023 International Search Report and Written Opinion dated Jul. 19, 2023.
PCT/US2023/025757 filed Jun. 20, 2023 International Search Report and Written Opinion dated Sep. 11, 2023.
U.S. Appl. No. 17/217,852, filed Mar. 30, 2021 Ex Parte Quayle Action dated Sep. 8, 2023.
U.S. Appl. No. 17/499,644, filed Oct. 12, 2021 Notice of Allowance dated Sep. 18, 2023.
U.S. Appl. No. 17/697,895, filed Mar. 17, 2022 Advisory Action dated Sep. 8, 2023.
U.S. Appl. No. 17/697,895, filed Mar. 17, 2022 Final Office Action dated Aug. 16, 2023.
PCT/US2022/024934 filed Apr. 14, 2022 International Search Report and Written Opinion dated Jul. 18, 2022.
PCT/US2023/027527 filed Jul. 12, 2023 International Search Report and Written Opinion dated Oct. 16, 2023.
U.S. Appl. No. 17/217,852, filed Mar. 30, 2021 Notice of Allowance dated Nov. 7, 2023.
U.S. Appl. No. 17/535,406, filed Nov. 24, 2021 Restriction Requirement dated Nov. 24, 2023.
U.S. Appl. No. 17/535,406, filed Nov. 24, 2021 Non-Final Office Action dated Feb. 15, 2024.
U.S. Appl. No. 17/689,773, filed Mar. 8, 2022 Non-Final Office Action dated Mar. 19, 2024.
U.S. Appl. No. 17/697,895, filed Mar. 17, 2022 Non-Final Office Action dated Jan. 11, 2024.
U.S. Appl. No. 17/731,155, filed Apr. 27, 2022 Restriction Requirement dated Feb. 28, 2024.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).
U.S. Appl. No. 17/696,675, filed Mar. 16, 2022 Non-Final Office Action dated Jun. 11, 2024.
U.S. Appl. No. 17/697,895, filed Mar. 17, 2022 Notice of Allowance dated May 8, 2024.
U.S. Appl. No. 17/725,394, filed Apr. 20, 2022 Non-Final Office Action dated Jun. 17, 2024.
U.S. Appl. No. 17/849,447, filed Jun. 24, 2022 Non-Final Office Action dated Apr. 10, 2024.
U.S. Appl. No. 18/524,620, filed Nov. 30, 2023 Non-Final Office Action dated Jun. 18, 2024.
PCT/US2023/015536 filed Mar. 17, 2023 International Preliminary Report on Patentability dated Sep. 10, 2024.
U.S. Appl. No. 17/191,551, filed Mar. 3, 2021 Non-Final Office Action dated Aug. 16, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Final Office Action dated Aug. 8, 2024.
U.S. Appl. No. 18/141,289, filed Apr. 28, 2023 Non-Final Office Action dated Sep. 28, 2024.
U.S. Appl. No. 18/524,620, filed Nov. 30, 2023 Notice of Allowance dated Sep. 12, 2024.
PCT/US2023/018076 filed Apr. 10, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/191,551, filed Mar. 3, 2021 Notice of Allowance dated Nov. 8, 2024.
U.S. Appl. No. 17/535,406, filed Nov. 24, 2021 Notice of Allowance dated Oct. 23, 2024.
U.S. Appl. No. 17/689,773, filed Mar. 8, 2022 Advisory Action dated Nov. 1, 2024.
U.S. Appl. No. 17/725,394, filed Apr. 20, 2022 Non-Final Office Action dated Nov. 19, 2024.
U.S. Appl. No. 17/849,447, filed Jun. 24, 2022 Advisory Action dated Oct. 24, 2024.
U.S. Appl. No. 17/863,211, filed Jul. 12, 2022 Restriction Requirement dated Nov. 15, 2024.

* cited by examiner

CATHETER WITH OPTIC SHAPE SENSING CAPABILITIES

PRIORITY

This application claims the benefit of priority to U.S. Provisional Application No. 62/983,396, filed Feb. 28, 2020, which is incorporated by reference in its entirety into this application.

BACKGROUND

In the past, certain intravascular guidance of medical instruments, such as guidewires and catheters for example, have used fluoroscopic methods for tracking placement of medical instruments. However, such fluoroscopic methods expose patients and their attending clinicians to harmful X-ray radiation. Moreover, in some cases, the patients are exposed to potentially harmful contrast media needed for the fluoroscopic methods.

Recently, electromagnetic tracking systems have been increasingly used in medical applications. Although electromagnetic tracking systems avoid line-of-sight reliance in tracking a catheter, these systems are prone to intermittent failures caused by electromagnetic field interference. More specifically, since electromagnetic tracking systems depend on the measurement of magnetic fields produced by field generators, these systems are susceptible to electromagnetic field interference from cellular telephones, tablets, laptops and other consumer electronics that emit electromagnetic waves. As a result, electromagnetic tracking systems are being subjected to more frequent signal dropouts and are defined to a limited depth range for signal retrieval.

Disclosed herein is a catheter with fiber optic shape sensing capabilities and methods of operation thereof, which is not subject to the disadvantages associated with electromagnetic tracking systems as described above.

BRIEF SUMMARY

Briefly summarized, embodiments disclosed herein are directed to a catheter featuring an elongated, integrated tubing, a septum (or septa), and a plurality of lumen formed between surfaces of the septum (or septa) and an inner surface of a wall of the integrated tubing (hereinafter, "tubing wall"). A plurality of micro-lumens are formed within the septum and within (or along) the tubing wall to retain a corresponding plurality of (optical) core fibers. According to one embodiment of the disclosure, each of the core fibers may constitute a single core grated fiber, namely a single light transmission medium such as a cylindrical element of glass or plastic with one or more sensors. Alternatively, according to another embodiment of the disclosure, each of the core fibers may constitute multiple (two or more) entwined transmission mediums with sensors.

More specifically, one embodiment of the catheter includes at least one septum spanning across a diameter of the integrated tubing and continuing longitudinally to subdivide an opening formed by the integrated tubing to produce two lumen. As described below, the septum may be fabricated with a first micro-lumen of the above-identified plurality of micro-lumens, where the first micro-lumen is coaxial with a central axis of the integrated tubing by being positioned within a medial portion of the septum at or near a cross-sectional center of the integrated tubing. The first micro-lumen is sized to retain a core fiber (hereinafter, "center core fiber"), where the diameter of the first micro-lumen may be sized to exceed the diameter of the center core fiber. In lieu of a single septum, the catheter may include two or more septa extending radially from the cross-sectional center to the tubing wall. Also, the first micro-lumen may be maintained by a protruding portion of the integrated tubing in lieu of the septum or in other deployments, provided the first micro-lumen is positioned coaxial with the central axis.

The tubing wall includes one or more micro-lumens, such as a second plurality of micro-lumens that are a subset of the above-identified plurality of micro-lumens. According to one embodiment of the disclosure, each of the second plurality of micro-lumens may be positioned at the same known radius from the cross-sectional center of the integrated tubing along a circumference of the tubing wall. For example, the second plurality of micro-lumens may be laterally aligned (e.g., oriented in parallel with the central axis) and axially positioned along the outer circumference of the tubing wall to retain a corresponding plurality of core fibers (hereinafter, "outer core fibers"). Alternatively, as described below in detail, the second plurality of micro-lumens may be laterally aligned and positioned with the outer core fibers being coextruded within the tubing wall.

The second plurality of micro-lumens, in accordance with one embodiment of the disclosure, are sized to retain a corresponding plurality of core fibers (hereinafter, "outer core fibers"), where the diameter of each of the second plurality of micro-lumens may also be sized larger than the diameter of the outer core fibers to provide "play" and isolate the core fibers from forces applied to the catheter surface, but would not be experienced by the core fibers. Such isolation may provide more accurate shaping sensing determinations as the measurement of (mechanical) strain experienced by the core fibers, may allow a medical instrument monitoring system to identify, with greater precision, shape or form changes to the catheter, and in particular the integrated tubing of the catheter.

According to one embodiment of the disclosure, when deployed as a single core grated fiber, the core fiber includes a plurality of sensors spatially distributed along its length between at least the proximal and distal ends of the integrated tubing. These distributed sensors may be deployed as an array of reflective gratings and positioned at a different region of the core fiber to enable distributed measurements throughout the entire length or a selected portion of the integrated tubing. These distributed measurements may be signal characteristics obtained from reflected light of different spectral widths (e.g., specific wavelength or specific wavelength ranges). On example of a reflected light characteristic may include a wavelength shift in the reflected light caused by strain (e.g., axial strain or other types of mechanical strain).

According to one embodiment of the disclosure, each sensor may constitute a reflective grating such as a fiber Bragg grating (FBG), namely an intrinsic sensor corresponding to a permanent, periodic refractive index change inscribed into the core fiber. Stated differently, the sensor operates as a light reflective mirror for a specific spectral width (e.g., a specific wavelength or specific range of wavelengths). As a result, as broadband incident light is supplied by an optical light source and propagates through a particular core fiber, upon reaching a first sensor of the distributed array of sensors for that core fiber, light of a prescribed spectral width associated with the first sensor is reflected back to an optical receiver within a console, including a display and the optical light source. The remaining spectrum of the incident light continues propagation through the core fiber toward a distal end of the integrated tubing. The remaining spectrum of the incident light may encounter other sensors from the distributed array of sensors, where each of these sensors is fabricated to reflect light with different specific spectral widths to provide distributed measurements, as described above.

During operation, multiple light reflections (also referred to as "reflected light signals") are returned to the console from each of the plurality of core fibers residing within the corresponding plurality of micro-lumens formed within the catheter. Each reflected light signal may be uniquely associated with a different spectral width. Information associated with the reflected light signals may be used to determine a three-dimensional representation of a physical state (e.g., shape length, shape, form, and/or orientation) of a portion of the catheter (e.g., tip, portion of tubing, etc.) or the catheter tubing in its entirety within the body of a patient (hereinafter, described as the "physical state of the catheter"). Herein, the outer core fibers are spatially separated along the circumference of the tubing wall and each outer core fiber is configured to separately return light of different spectral widths (e.g., specific light wavelength or a range of light wavelengths) reflected from the distributed array of sensors fabricated in each of the core fibers. A comparison of detected shifts in wavelength of the reflected light from the outer core fibers to wavelength shifts of the reflected light from the center core fiber, operating as a reference, may be used to determine the physical state of the catheter.

More specifically, during vasculature insertion, the clinician may rely on the console to visualize a current physical state of the catheter (e.g., shape, orientation, etc.) to avoid potential path deviations that would be caused by changes in catheter orientation (e.g., changes in angular orientation of the integrated tubing, etc.). As the outer core fibers reside within the second plurality of micro-lumens laterally aligned at different locations along the circumference of the tubing wall, changes in angular orientation (bending) of the integrated tubing of the catheter imposes different types (e.g., compression or tension) and degrees of strain on each of the outer core fibers as well as the center core fiber. The different types and/or degree of strain may cause the sensors of the core fibers to apply different wavelength shifts, which can be measured to extrapolate the physical state of the catheter.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Figure 1:
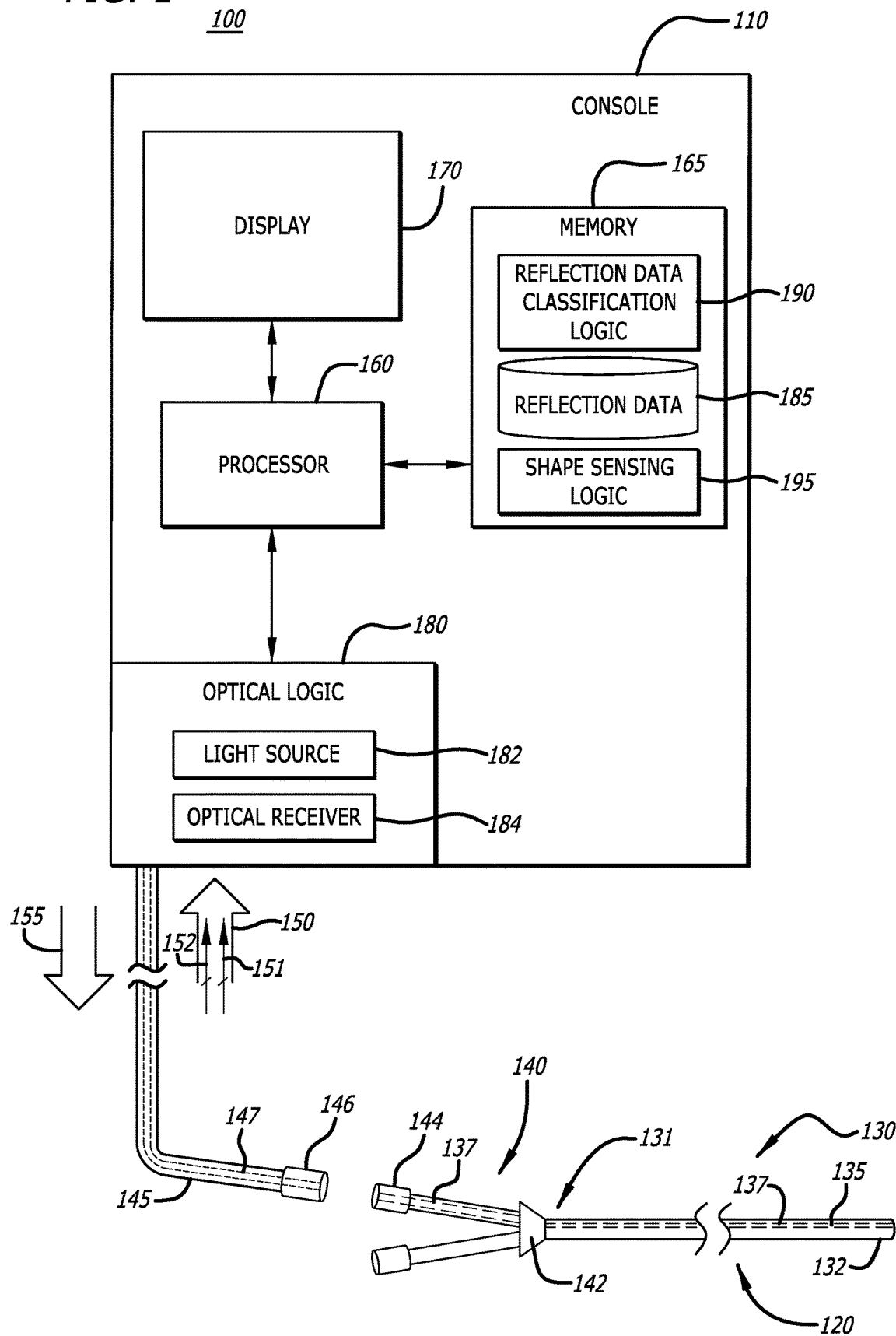
FIG. 1 is an illustrative embodiment of a medical instrument monitoring system with a medical instrument with optic shape sensing capabilities.

Reference will now be made to figures wherein like structures will be provided with like reference designations. It is understood that the drawings are diagrammatic and schematic representations of exemplary embodiments of the invention, and are neither limiting nor necessarily drawn to scale.

Regarding terms used herein, it should be understood the terms are for the purpose of describing some particular embodiments, and the terms do not limit the scope of the concepts provided herein. Ordinal numbers (e.g., first, second, third, etc.) are generally used to distinguish or identify different components or operations, and do not supply a serial or numerical limitation. For example, "first," "second," and "third" components or operations need not necessarily appear in that order, and the particular embodiments including such components or operations need not necessarily be limited to the three components or operations. Similarly, labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The term "logic" is representative of hardware and/or software that is configured to perform one or more functions. As hardware, logic may include circuitry having data processing and/or storage functionality. Examples of such circuitry may include, but are not limited or restricted to a processor, a programmable gate array, a microcontroller, an application specific integrated circuit, combinatorial circuitry, or the like. Alternatively, or in combination with the hardware circuitry described above, the logic may be software in the form of one or more software modules, which may be configured to operate as its counterpart circuitry. The software modules may include, for example, an executable application, a daemon application, an application programming interface (API), a subroutine, a function, a procedure, a routine, source code, or even one or more instructions. The software module(s) may be stored in any type of a suitable non-transitory storage medium, such as a programmable circuit, a semiconductor memory, non-persistent storage such as volatile memory (e.g., any type of random access memory "RAM"), persistent storage such as non-volatile memory (e.g., read-only memory "ROM", power-backed RAM, flash memory, phase-change memory, etc.), a solid-state drive, hard disk drive, an optical disc drive, or a portable memory device.

For clarity, it is to be understood that the word "proximal" refers to a direction relatively closer to a clinician using the device to be described herein, while the word "distal" refers to a direction relatively further from the clinician. Herein, the "proximal portion" of an integrated tubing of a catheter disclosed herein, for example, includes a portion of the catheter tubing intended to be near a clinician when the catheter is used on the patient. Likewise, a "proximal end" of the catheter tubing, for example, includes an end intended to be near the clinician when the catheter is in use. The proximal portion of the catheter tubing may include the proximal end of the catheter tubing; however, proximal portion of the catheter tubing does not need to include the proximal end of the catheter tubing.

Similarly, a "distal portion" of the integrated tubing of the catheter includes a portion of the catheter tubing intended to be near or in a patient when the catheter is used on the patient. Likewise, a "distal end" of the catheter tubing includes an end of the catheter tubing intended to be near or in the patient when the catheter is in use. The distal portion of the catheter tubing can include the distal end of the catheter tubing; however, the distal portion of the catheter tubing does not need include the distal end of the catheter tubing. Also, the words "including," "has," and "having," as used herein, including the claims, shall have the same meaning as the word "comprising."

Unless defined otherwise, all technical and scientific terms used herein have the same meaning as commonly understood by those of ordinary skill in the art.

Referring to FIG. 1, an exemplary embodiment of a medical instrument monitoring system 100 is shown. Herein, the medical instrument monitoring system 100 features a console 110 and a medical instrument 120 communicatively coupled to the console 110. For this embodiment, the medical instrument 120 corresponds to a catheter, which features an integrated tubing 130 with two or more lumen 135 extending between a proximal end 131 and a distal end 132 of the integrated tubing 130. The integrated tubing 130 (sometimes referred to as "catheter tubing") is in communication with one or more extension legs 140 via a bifurcation hub 142. An optical-based catheter connector 144 may be included on a proximal end of at least one of the extension legs 140 to enable the catheter 120 to operably connect to the console 110 via an interconnect 145 or another suitable component. Herein, the interconnect 145 may include a connector 146 that, when coupled to the optical-based catheter connector 144, establishes optical connectivity between one or more optical fibers 147 (hereinafter, "optical fiber(s)") included as part of the interconnect 145 and core fibers 137 deployed within the catheter 120 and integrated into the tubing 130. Alternatively, a different combination of connectors, including one or more adapters, may be used to optically connect the optical fiber(s) 147 to the core fibers 137 within the catheter 120.

An exemplary implementation of the console 110 includes a processor 160, a memory 165, a display 170 and optical logic 180, although it is appreciated that the console 110 can take one of a variety of forms. The processor 160, with access to the memory 165 (e.g., non-volatile memory), is included to control functionality of the console 110 during operation. As shown, the display 170 may be a liquid crystal diode (LCD) display integrated into the console 110 and employed as a user interface to display information to the clinician, especially during a catheter placement procedure (e.g., cardiac catheterization). In another embodiment, the display 170 may be separate from the console 110. For both of these embodiments, the content rendered by the display 170 may constitute a two-dimensional (2-D) or three-dimensional (3-D) representation of the physical state of the catheter 120 (e.g., length, shape, form, and/or orientation of the catheter 120 or a portion of the catheter 120) computed from characteristics of reflected light signals 150 returned to the console 110. According to one embodiment of the disclosure, the reflected light signals 150 may pertain to various discrete portions (e.g., specific spectral widths) of broadband incident light 155 transmitted from and sourced by the optical logic 180, as described below.

Referring still to FIG. 1, the optical logic 180 is configured to support graphical rendering of the catheter 120, most notably the integrated tubing 130 of the catheter 120, based on characteristics of the reflected light signals 150 received from the catheter 120. The characteristics may include shifts in wavelength caused by strain on certain regions of the core fibers 137 integrated within (or along) a wall of the integrated tubing 130, which may be used to determine (through computation or extrapolation of the wavelength shifts) the physical state of the catheter 120, notably its integrated tubing 130 or a portion of the integrated tubing 130 such as a tip or distal end of the tubing 130 to read fluctuations (real-time movement) of the tip (or distal end).

More specifically, the optical logic 180 includes a light source 182. The light source 182 is configured to transmit the broadband incident light 155 for propagation over the optical fiber(s) 147 included in the interconnect 145, which are optically connected to multiple core fibers 137 within the catheter tubing 130. In one embodiment, the light source 182 is a tunable swept laser, although other suitable light source can also be employed in addition to a laser, including semi-coherent light sources, LED light sources, etc.

According to one embodiment of the disclosure, the optical logic 180 further includes an optical receiver 184 (e.g., a photodetector such as a positive-intrinsic-negative "PIN" photodiode, avalanche photodiode, etc.). Herein, the optical receiver 184 is configured to: (i) receive returned optical signals, namely reflected light signals 150 received from optical fiber-based reflective gratings (sensors) fabricated within each of the core fibers 137 deployed within the catheter 120 (see FIG. 3B), and (ii) translate the reflected light signals 150 into reflection data 185, namely data in the form of electrical signals representative of the reflected light signals including wavelength shifts caused by strain. The reflected light signals 150 associated with different spectral widths include reflected light signals 151 provided from sensors positioned in the center core fiber (reference) of the catheter 120 and reflected light signals 152 provided from sensors positioned in the outer core fibers of the catheter 120, as described below.

As shown, both the light source 182 and the optical receiver 184 are operably connected to the processor 160, which governs their operation. Also, the optical receiver 184 is operably coupled to provide the reflection data 185 to the memory 165 for storage and processing by reflection data classification logic 190. The reflection data classification logic 190 may be configured to (i) identify which core fibers pertain to which of the received reflection data 185 and (ii) segregate the reflection data 185 provided from reflected light signals 150 pertaining to similar regions of the catheter 120 and/or spectral widths into analysis groups. The reflection data for each analysis group is made available to shape sensing logic 195 for analytics.

According to one embodiment of the disclosure, the shape sensing logic 195 is configured to compare wavelength shifts measured by sensors deployed in each outer core fiber at the same measurement region of the catheter (or same spectral width) to the wavelength shift at the center core fiber positioned along central axis and operating as a neutral axis of bending. From these analytics, the shape sensing logic 190 may determine the shape the core fibers have taken in 3-D space and may further determine the current physical state of the catheter 120 in 3-D space for rendering on the display 170.

According to one embodiment of the disclosure, the shape sensing logic 195 may generate a rendering of the current physical state of the catheter 120, especially the integrated tubing 130, based on heuristics or run-time analytics. For example, the shape sensing logic 195 may be configured in accordance with machine-learning techniques to access a data store (library) with pre-stored data (e.g., images, etc.) pertaining to different regions of the catheter 120 in which the core fibers 137 experienced similar or identical wavelength shifts. From the pre-stored data, the current physical state of the catheter 120 may be rendered. Alternatively, as another example, the shape sensing logic 195 may be configured to determine, during run-time, changes in the physical state of each region of the catheter 120, notably the tubing 130, based on at least (i) resultant wavelength shifts experienced by the core fibers 137 and (ii) the relationship of these wavelength shifts generated by sensors positioned along different outer core fibers at the same cross-sectional region of the catheter 120 to the wavelength shift generated by a sensor of the center core fiber at the same cross-sectional region. It is contemplated that other processes and procedures may be performed to utilize the wavelength shifts as measured by sensors along each of the core fibers 137 to render appropriate changes in the physical state of the catheter 120.

Figure 2:
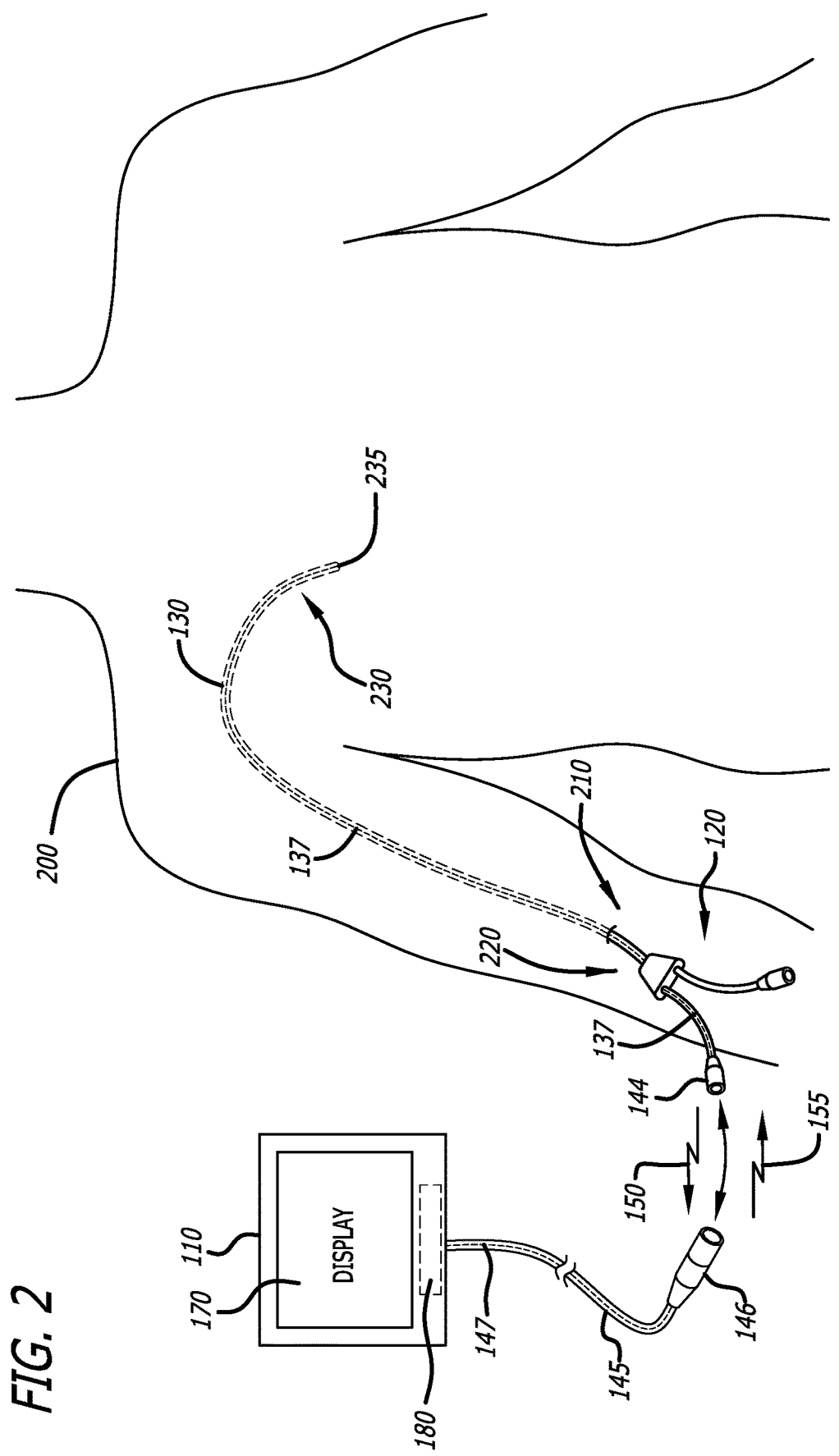
FIG. 2 is an exemplary embodiment of the medical instrument monitoring system of FIG. 1 during operation and insertion of the catheter into a patient.

Referring now to FIG. 2, an embodiment of the catheter 120 illustrating its insertion into a vasculature of a patient 200 through a skin insertion site 210 is shown. Herein, the catheter 120 generally includes the integrated tubing 130 with a proximal portion 220 that generally remains exterior to the patient 200 and a distal portion 230 that generally resides within the patient vasculature after placement is complete. The (integrated) catheter tubing 130 may be advanced to a desired position within the patient vasculature such as a distal end (or tip) 235 of the catheter tubing 130 is proximate the patient's heart, such as in the lower one-third (⅓) portion of the Superior Vena Cava ("SVC") for example. For this embodiment, various instruments may be placed at the distal end 235 of the catheter tubing 130 to measure pressure of blood in a certain heart chamber and in the blood vessels, view an interior of blood vessels, or the like.

During advancement through a patient vasculature, the catheter tubing 130 receives broadband incident light 155 from the console 110 via optical fiber(s) 147 within the interconnect 145, where the incident light 155 propagates to the core fibers 137 within the catheter tubing 130. According to one embodiment of the disclosure, the connector 146 of the interconnect 145 terminating the optical fiber(s) 147 may be coupled to the optical-based catheter connector 144, which may be configured to terminate the core fibers 137 deployed within the catheter 120. Such coupling optically connects the core fibers 137 of the catheter 120 with the optical fiber(s) 147 within the interconnect 145. The optical connectivity is needed to propagate the incident light 155 to the core fibers 137 and return the reflected light signals 150 to the optical logic 180 within the console 110 over the interconnect 145. As described below in detail, the physical state of the catheter 120 may be ascertained based on analytics of the wavelength shifts of the reflected light signals 150.

Figure 3A:
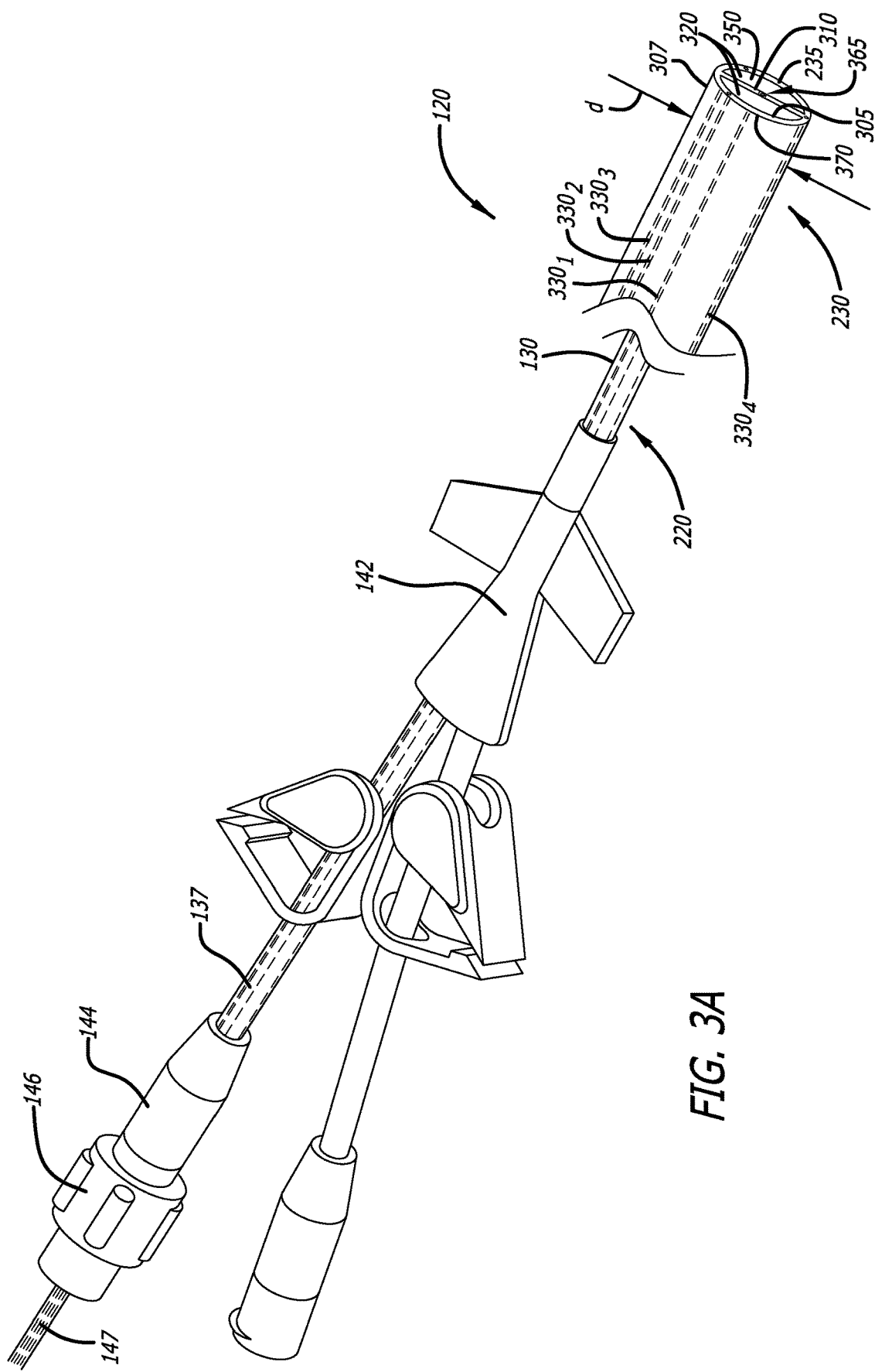
FIG. 3A is an illustrative embodiment of the catheter of FIGS. 1-2.

Referring to FIG. 3A, an illustrative embodiment of the catheter 120 of FIGS. 1-2 is shown. Herein, the catheter 120 includes the integrated tubing 130 and at least one septum 310 extending across a diameter "d" of the tubing 130 and positioned at distal end 235 of the catheter tubing 130. The septum(s) 310 assist in forming multiple lumina 320 within the tubing 130 between an inner surface 305 of a wall 300 forming the tubing 130 and surfaces of the septum 310 extending longitudinally from the distal end 235 towards the bifurcation hub 142 of the catheter 120. Sized with a diameter less than any of the multiple lumina 320 (e.g., lumen 400 and 410 of FIG. 4A), a plurality of micro-lumens $330_1$-$330_N$ (N>3) may be collectively formed within the septum 310 and along a circumference of the catheter tubing 130, such as formed in the wall 300 of the integrated tubing 130 itself (e.g., one or more micro-lumens, such as micro-lumens $330_2$-$330_4$, fabricated to reside between the inner surface 305 and an outer surface 307 of the wall 300) or as a longitudinal bead 405 formed on the inner surface 305 or a longitudinal bead 407 formed on the outer surface 307 of the wall 300 (see FIG. 4A). The micro-lumens $330_1$-$330_N$ are configured to retain a corresponding plurality of core fibers $340_1$-$340_N$, as shown in FIG. 3B.

Figure 3B:
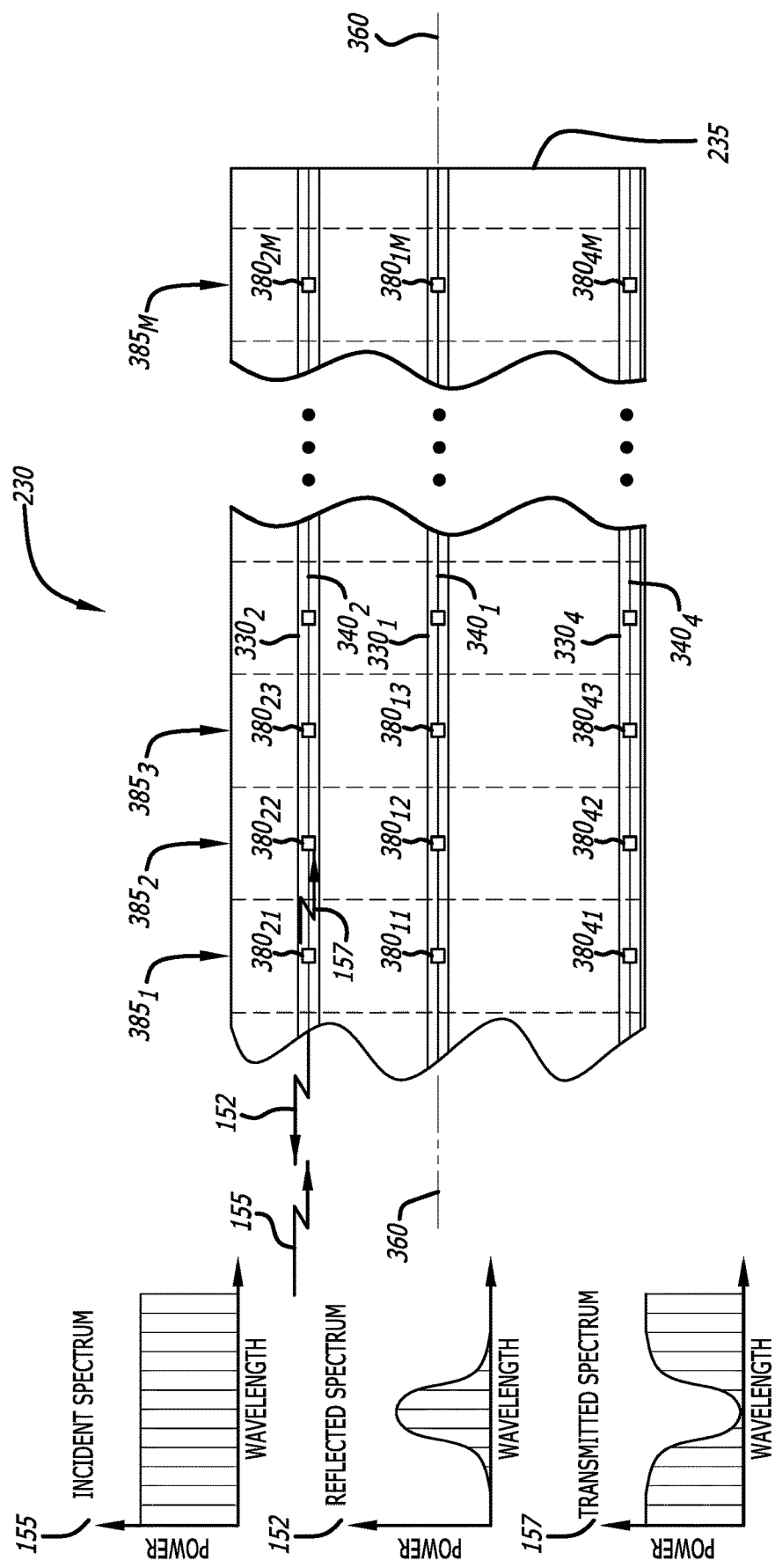
FIG. 3B is an illustrative embodiment of the micro-lumen and core fiber deployment within the integrated tubing of the catheter shown in FIG. 3A.

More specifically, as show in FIGS. 3A-3B, the catheter 120 includes at least one septum (e.g., septum 310) spanning across the diameter "d" of the tubing 130 and continuing longitudinally to subdivide an opening 350 formed by the tubing 130 to produce the lumina 320. The septum 310 may be fabricated as part of the catheter 120 during extrusion or may be fabricated as a separate component and inserted into the tubing of the catheter during manufacture. As an alternative embodiment, the catheter 120 may be configured where the septum 310 does not divide the opening 350, as portion of the wall 300 may protrude into the cross section space occupied by the distal end of the catheter (area at the opening 350) or portion of the wall 300 may protrude into the cross section space occupied by the distal end of the catheter (area at the opening 350) in which a center micro-lumen $300_1$ is formed within the protruding portion of the wall 300 to maintain one or more core fibers.

As described below, the septum 310 is fabricated with a first micro-lumen $330_1$ of the above-identified plurality of micro-lumens $330_1$-$330_N$, where the first micro-lumen $330_1$ is coaxial with a central axis 360 of the integrated tubing 130 by being positioned within a medial portion of the septum 310 at or near a cross-sectional center 365 of the integrated tubing 130. The cross-sectional center 365 is the center location from a perspective facing a cross-sectional area of the distal end 235 of the integrated tubing 130. Herein, the first micro-lumen $330_1$ is configured to retain a single core fiber $340_1$ (hereinafter, "center core fiber"). A second plurality of micro-lumens $330_2$-$330_N$, which are a subset of the plurality of micro-lumens $330_1$-$330_N$, are positioned along a circumference 370 of the integrated tubing 130. The micro-lumens $330_2$-$330_N$ retain corresponding core fibers $340_2$-

$340_N$ (hereinafter, "outer core fibers"). According to one embodiment of the disclosure, as shown, one or more of the outer core fibers (e.g., the second plurality of core fibers $340_2$-$340_N$) are located at different quadrants along the circumference 370 of the integrated tubing 130 as shown in FIG. 4B.

As shown in FIG. 3B, each core fiber $340_i$ ($1 \le i \le N$) includes an array of sensors $380_{i1}$-$380_{iM}$ ($1 \le i \le N$; $M \ge 2$) spatially distributed along its length between at least a proximal and distal ends of the catheter tubing 130. Each sensor $380_{i1}$-$380_{iM}$ may be positioned at different measurement regions $385_1$-$385_M$ distributed along a prescribed length of the core fiber 340; in efforts to sense strain occurring at these fiber regions $385_1$-$385_M$, especially during advancement of the catheter 120 within the patient vasculature. The distribution length may be static or variable.

More specifically, each of the sensors $380_{i1}$-$380_{iM}$ (i=1 ... N as shown in FIG. 3B) is configured to reflect light at a different spectral width (e.g., specific wavelength or specific wavelength range), where neighboring sensors (e.g., sensors $380_{i1}$-$380_{i2}$, sensors $380_{i2}$-$380_{i3}$, etc.) may be arranged to reflect light with non-overlapping spectral widths. However, in response to the core fiber $340_2$ (i=2) experiencing strain at any of the fiber regions $385_1$-$385_M$ (e.g., fiber regions $385_1$), the sensor $380_{21}$ also experiences strain that causes the sensor $380_{21}$ to alters characteristics of the reflected light signal in order to represent the sensed strain. As a result, collectively, the reflected light signals returned by sensors $380_{i1}$-$380_{iM}$ along each core fiber $340_1$-$340_N$ may be used by the console 110 to recover reflection data for use in determining the current 3-D shape of the core fibers $340_1$-$340_N$. From the current 3-D shape of the core fibers $340_1$-$340_N$, the current 3-D shape of the catheter 120 may be determined for subsequent rendering.

For ease of discussion, the operations of a selected core fiber $340_2$ and the operations of the sensors $380_{21}$-$380_{2M}$ deployed on the core fiber $340_2$ shall be discussed. The other core fibers $340_1$, $340_3$ ... and/or $340_N$ may be configured in a similar or identical manner.

According to one embodiment of the disclosure, each sensor $380_{21}$-$380_{2M}$ may be configured as a fiber Bragg grating (FBG), namely an intrinsic sensor corresponding to a permanent, periodic refractive index change inscribed into the core fiber $340_2$. Stated differently, each sensor $380_{21}$ ... and $380_{2M}$ operates as a light reflective mirror for a different, specific spectral width. As a result, as broadband incident light 155 is supplied by an optical light source and propagates through the core fiber $340_2$, upon reaching a first sensor $380_{21}$ positioned at a first region $385_1$ of the core fiber $340_2$, light 152 of a spectral width selected for the first sensor $380_{21}$ is reflected back to the optical receiver 184 within the console 110 (see FIG. 1). Based on the type and degree of strain (e.g., compression or tension) sensed on the core fiber $340_2$ at the first region $385_1$, the first sensor $380_{21}$ alters characteristics of reflected light signal 152. The altered characteristics may correspond to the reflected light signal 152 experiencing a wavelength shift that is correlated to the type of strain (e.g., compression or tension) and degree of strain. The remaining spectrum 157 of the incident light 155 continues propagation through the core fiber $340_2$ toward the distal end 235 of the catheter tubing 130. The remaining spectrum 157 of the incident light 155 may encounter another sensor $380_{22}$ ... or $380_{2M}$, where each of these sensors $380_{22}$ ... or $380_{2M}$ is fabricated to reflect light with different specific spectral widths. Similarly, reflected light signals of the different spectral widths are returned from the core fiber $340_2$.

As an illustrative example, where a particular region of the catheter 120 is undergoing a change in angular orientation (e.g., catheter tubing 130 is bending), a portion of the second outer core fiber $340_2$, which is located at the first measurement region $385_1$, may experience tension (positive strain; force applied to increase length). As a result, upon receipt of the incident light 155, the sensor $380_{21}$ located at the first region $385_1$ would return reflected light 152 with an elevated attenuation (e.g., frequency of the reflected light signal 152 is higher than the frequency of the incident light 155). Therefore, the tension applied to the second outer core fiber $340_2$ causes a shift (increase) in the reflected light wavelength and amount of wavelength shift is correlated to the amount of tension applied to the second outer core fiber $340_2$.

Similarly, as the particular region of the catheter is undergoing the change in angular orientation, a portion of a fourth outer core fiber $340_4$ also located in the first measurement region $385_1$, may experience compression (negative strain; force applied to shorten length). As a result, upon receipt of the incident light 155, the sensor $380_{41}$ located at the first region $385_1$ would return reflected light 152 with a decreased attenuation (e.g., frequency of the reflected light signal 152 is lower than the frequency of the incident light 155). Therefore, the tension applied to the fourth outer core fiber $340_4$ causes a shift (decrease) in the reflected light wavelength and amount of wavelength shift conducted on the reflected light signal 152 is correlated to the amount of compression applied to the fourth outer core fiber $340_4$.

In view of the foregoing, different strains effect the plurality of core fibers $340_1$-$340_N$ differently, given their longitudinal position within spatially separated micro-lumens $330_1$-$330_N$. The degrees of wavelength shift encountered by different sensors along a distributed array of sensor for each core fiber $340_1$-$340_N$ may collectively identify the type (e.g., compression, tension) and amount of strain imposed on each region of the plurality of core fibers. Hence, multiple reflected light signals corresponding to the different spectral widths, which are produced by the distributed array of sensors positioned at selected regions over a length of the core fiber, may be provide 3-D shape sensing information for the shape sensing logic 195 within the console 110 to determine how each of the monitored regions of the catheter 120 is being manipulated. As a result, the current physical state of the catheter 120 may be determined and rendered in three-dimension (3-D) on the display 165 of the console 110 based on analytics of the wavelength shifts provided from the core fibers, as described above.

Figure 4A:
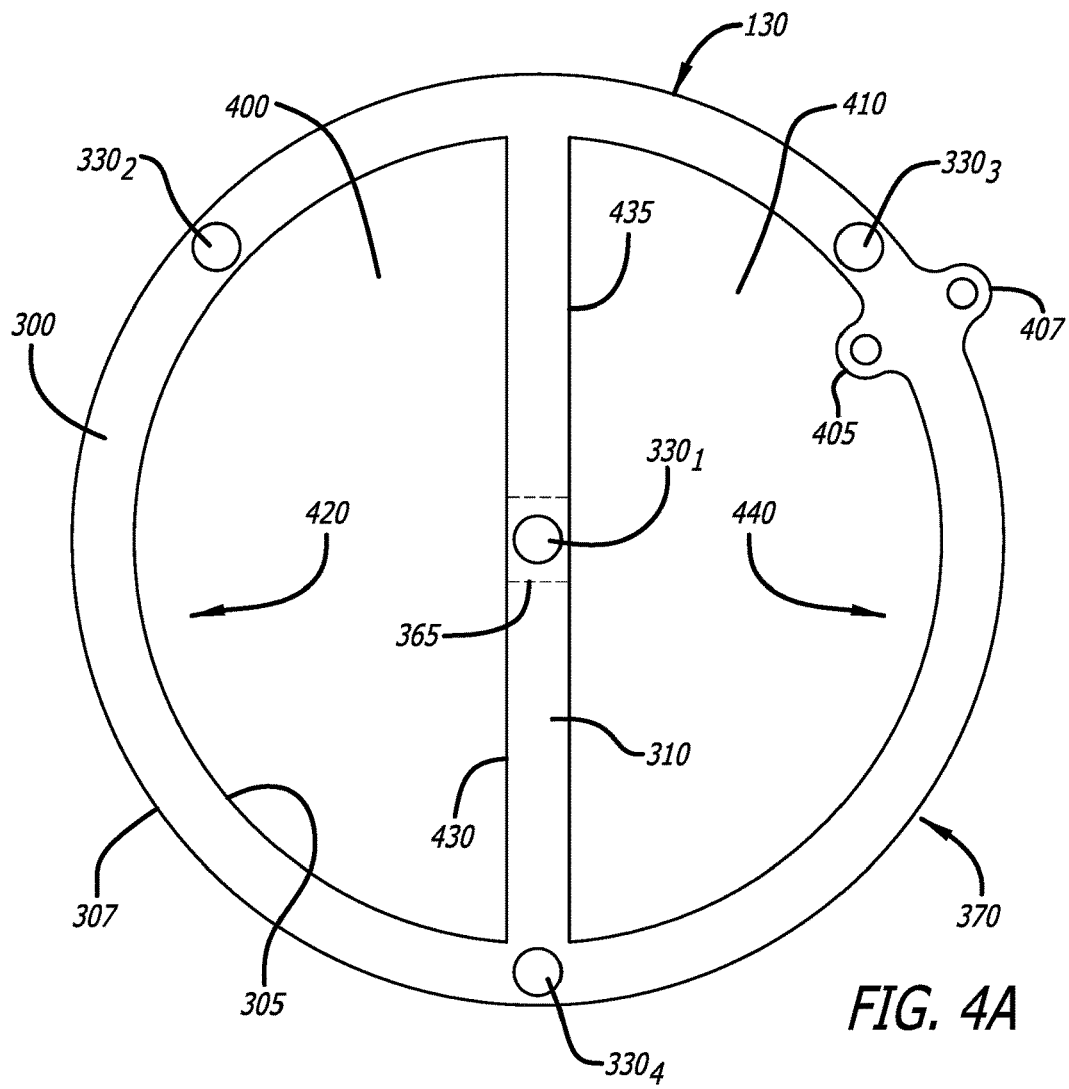
FIG. 4A is a perspective view of a first illustrative embodiment of the catheter of FIGS. 3A-3B including the integrated tubing, a diametrically disposed septum, and micro-lumens formed within the tubing and septum.
Figure 4B:
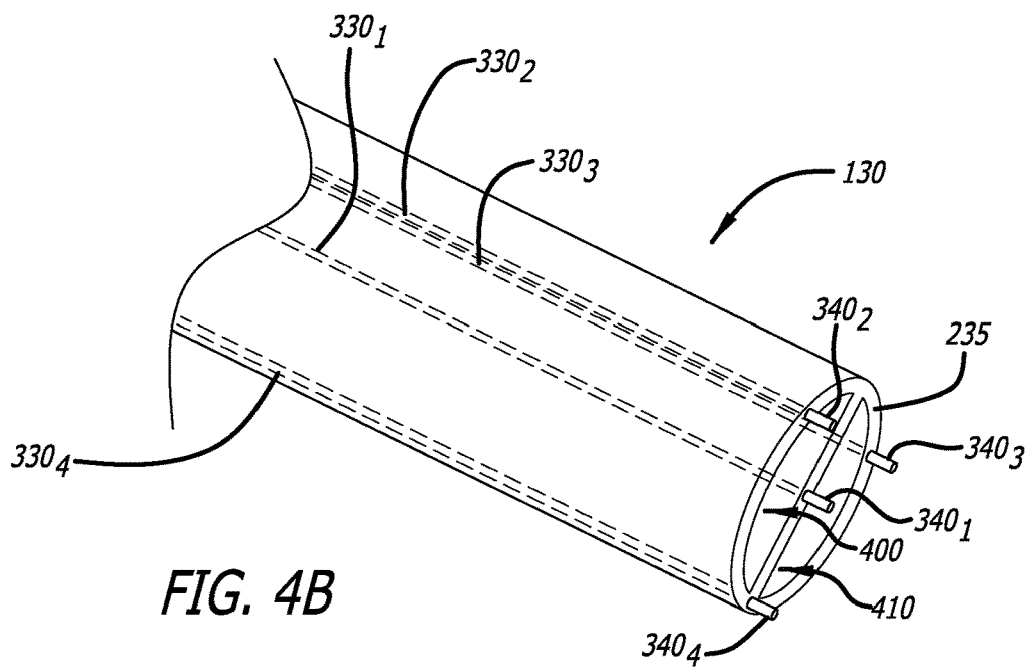
FIG. 4B is a perspective view of the first illustrative embodiment of the catheter of FIG. 4A including core fibers installed within the micro-lumens.

Referring now to FIG. 4A, a perspective view of a first illustrative embodiment of the integrated tubing 130 of the catheter 120 of FIGS. 3A-3B is shown. Herein, the catheter 120 includes the integrated tubing 130, the diametrically disposed septum 310, and the plurality of micro-lumens $330_1$-$330_4$ which, for this embodiment, are fabricated to reside within the wall 300 of the integrated tubing 130 and within the septum 310. In particular, the septum 310 separates a single lumen, formed by the inner surface 305 of the wall 300 of the tubing 130, into multiple lumen, namely two lumen 400 and 410 as shown. Herein, the first lumen 400 is formed between a first arc-shaped portion 420 of the inner surface 305 of the wall 300 forming the tubing 130 and a first outer surfaces 430 of the septum 310 extending longitudinally within the tubing 130. The second lumen 410 is formed between a second arc-shaped portion 440 of the inner surface 305 of the wall 300 forming the tubing 130 and a second outer surfaces 435 of the septum 310.

According to one embodiment of the disclosure, the two lumen 400 and 410 have approximately the same volume. However, the septum 310 need not separate the tubing 130 into two equal lumen. For example, instead of the septum 310 extending vertically (12 o'clock to 6 o'clock) from a front-facing, cross-sectional perspective of the tubing 130, the septum 310 could extend horizontally (3 o'clock to 9 o'clock), diagonally (1 o'clock to 7 o'clock; 10 o'clock to 4 o'clock) or angularly (2 o'clock to 10 o'clock). In the later configuration, each of the lumens 400 and 410 of the tubing 130 would have a different volume.

With respect to the plurality of micro-lumens $330_1$-$330_4$, the first micro-lumen $330_1$ is fabricated within the septum 310 at or near the cross-sectional center 365 of the tubing 130. For this embodiment, three micro-lumens $330_2$-$330_4$ are fabricated to reside within the wall 300 of the tubing 130. In particular, a second micro-lumen $330_2$ is fabricated within the wall 300 of the tubing 310, namely between the inner surface 305 and outer surface 307 of the first arc-shaped portion 420 of the wall 300. Similarly, the third micro-lumen $330_3$ is also fabricated within the wall 300 of the tubing 310, namely between the inner and outer surfaces 305/307 of the second arc-shaped portion 430 of the wall 300. The fourth micro-lumen $330_4$ is also fabricated within the inner and outer surfaces 305/307 of the wall 300 that are aligned with the septum 310.

According to one embodiment of the disclosure, as shown in FIG. 4A, the micro-lumens $330_2$-$330_4$ are positioned in accordance with a "top-left" (10 o'clock), "top-right" (2 o'clock) and "bottom" (6 o'clock) layout from a front-facing, cross-sectional perspective. Of course, the micro-lumens $330_2$-$330_4$ may be positioned differently, provided that the micro-lumens $330_2$-$330_4$ are spatially separated along the circumference 370 of the tubing 130 to ensure a more robust collection of reflected light signals from the outer core fibers $340_2$-$340_4$ when installed. For example, two or more of micro-lumens (e.g., micro-lumens $330_2$ and $330_4$) may be positioned at different quadrants along the circumference 370 of the catheter wall 300.

Referring now to FIG. 4B, a perspective view of the first illustrative embodiment of the integrated tubing 130 of the catheter 120 of FIG. 4A is shown, with the core fibers $340_1$-$340_4$ installed within the micro-lumens $330_1$-$330_4$. According to one embodiment of the disclosure, the second plurality of micro-lumens $330_2$-$330_4$ are sized to retain corresponding outer core fibers $340_2$-$340_4$, where the diameter of each of the second plurality of micro-lumens $330_2$-$330_4$ may be sized just larger than the diameters of the outer core fibers $340_2$-$340_4$. The size differences between a diameter of a single core fiber and a diameter of any of the micro-lumen $330_1$-$330_4$ may range between 0.001 micrometers (μm) and 1000 μm, for example. As a result, the cross-sectional areas of the outer core fibers $340_2$-$340_4$ would be less than the cross-sectional areas of the corresponding micro-lumens $330_2$-$330_4$. A "larger" micro-lumen (e.g., micro-lumen $330_2$) may better isolate external strain being applied to the outer core fiber $340_2$ from strain directly applied to the tubing 130 itself. Similarly, the first micro-lumen $330_1$ may be sized to retain the center core fiber $340_1$, where the diameter of the first micro-lumen $330_1$ may be sized just larger than the diameter of the center core fiber $340_1$.

As an alternative embodiment of the disclosure, one or more of the micro-lumens $330_1$-$330_4$ may be sized with a diameter that exceeds the diameter of the corresponding one or more core fibers $340_1$-$340_4$. However, at least one of the micro-lumens $330_1$-$330_4$ is sized to fixedly retain their corresponding core fiber (e.g., core fiber retained with no spacing between its lateral surface and the interior wall surface of its corresponding micro-lumen). As yet another alternative embodiment of the disclosure, all the micro-lumens $330_1$-$330_4$ are sized with a diameter to fixedly retain the core fibers $340_1$-$340_4$.

Figure 5:
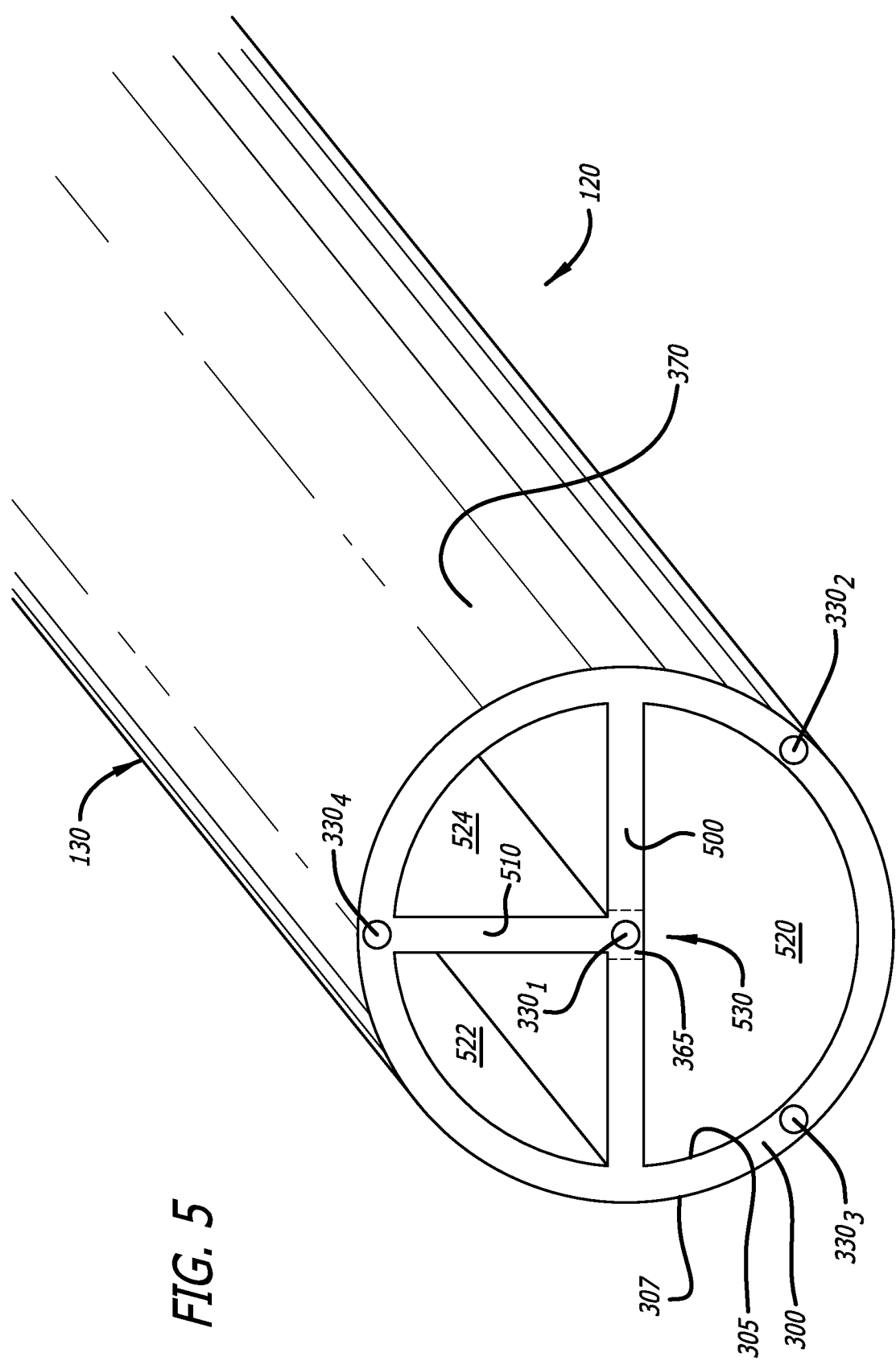
FIG. 5 is a perspective view of second illustrative embodiment of the catheter of FIGS. 3A-3B including the integrated tubing, a diametrically disposed septum, a radially disposed septum, and micro-lumens formed within the tubing and septum.

Referring to FIG. 5, a perspective view of second illustrative embodiment of the catheter 120 of FIGS. 3A-3B is shown. The catheter 120 includes the integrated tubing 130 and a diametrically disposed septum 500 along with a radially disposed septum 510 extending from a cross-sectional center 365 of the integrated tubing 130. Each of the three lumens 520, 522, and 524 is further defined at least in part by the septum 500. Each lumen of the two lumens 522 and 524 is even further defined at least in part by the septum 510. As shown, the septum 500 separates the interior space within the tubing 130 into a first set of semi-circular lumens, including the first lumen 520. The septum 510 further separates one of the first set of semi-circular lumens into lumens 522 and 524. As a result, the second lumen 522 may be configured with approximately the same volume as the third lumen 524, and the first lumen 520 may be configured with at least double the volume of the second and third lumen 522 and 524, provided the longitudinal lengths of these lumen 520, 522, 524 are equivalent.

As further shown in FIG. 5, the plurality of micro-lumens $330_1$-$330_4$ are fabricated to be located within the wall 300 of the integrated tubing 130 and within the septum 500. As similar to FIG. 4A, the first micro-lumen $330_1$ is fabricated within a medial portion 530 of the septum 500 at or near the cross-sectional center 365 of the integrated tubing 130. The three micro-lumens $330_2$-$330_4$ are fabricated to reside within the wall 300 of the integrated tubing 130. In particular, a second micro-lumen $330_2$ is fabricated within the wall 300 of the tubing 310, namely between the inner surface 305 and the outer surface 307 of the wall 300 defining the first lumen 520. Similarly, the third micro-lumen $330_3$ is also fabricated within the wall 300 of the tubing 310, such as within another area of the wall 300 between its inner surface 305 and outer surface 307. Extending in radial directions from the cross-sectional center 365, the third micro-lumen $330_3$ is displaced approximately ninety radial degrees) (90° or more from the second micro-lumen $330_2$. The fourth micro-lumen $330_4$ may be fabricated within the inner surface 305 and the outer surface 307 of the wall 300, where the fourth micro-lumen $330_4$ is aligned with the septum 510. Alternatively, the fourth micro-lumen $330_4$ may be fabricated within septum 510 substantially closer to the inner surface 305 of the wall 300 than the cross-sectional center 365.

According to this particular embodiment of the disclosure, the micro-lumens $330_2$-$330_4$ are positioned in accordance with a "bottom-right" (4 o'clock), "bottom-left" (8 o'clock) and "top" (12 o'clock) layout from a front-facing, cross-sectional perspective. Of course, the micro-lumens $330_2$-$330_4$ may be positioned differently, provided that the micro-lumens $330_2$-$330_4$ are spatially separated along the circumference 370 of the tubing 130 to ensure a more robust collection of reflected light signals from the outer core fibers $340_2$-$340_4$ when installed. For example, as shown, at least two different micro-lumens (e.g., micro-lumens $330_2$ and $330_3$) may be positioned at different quadrants along the circumference 370 of the catheter wall 300.

Figure 6A:
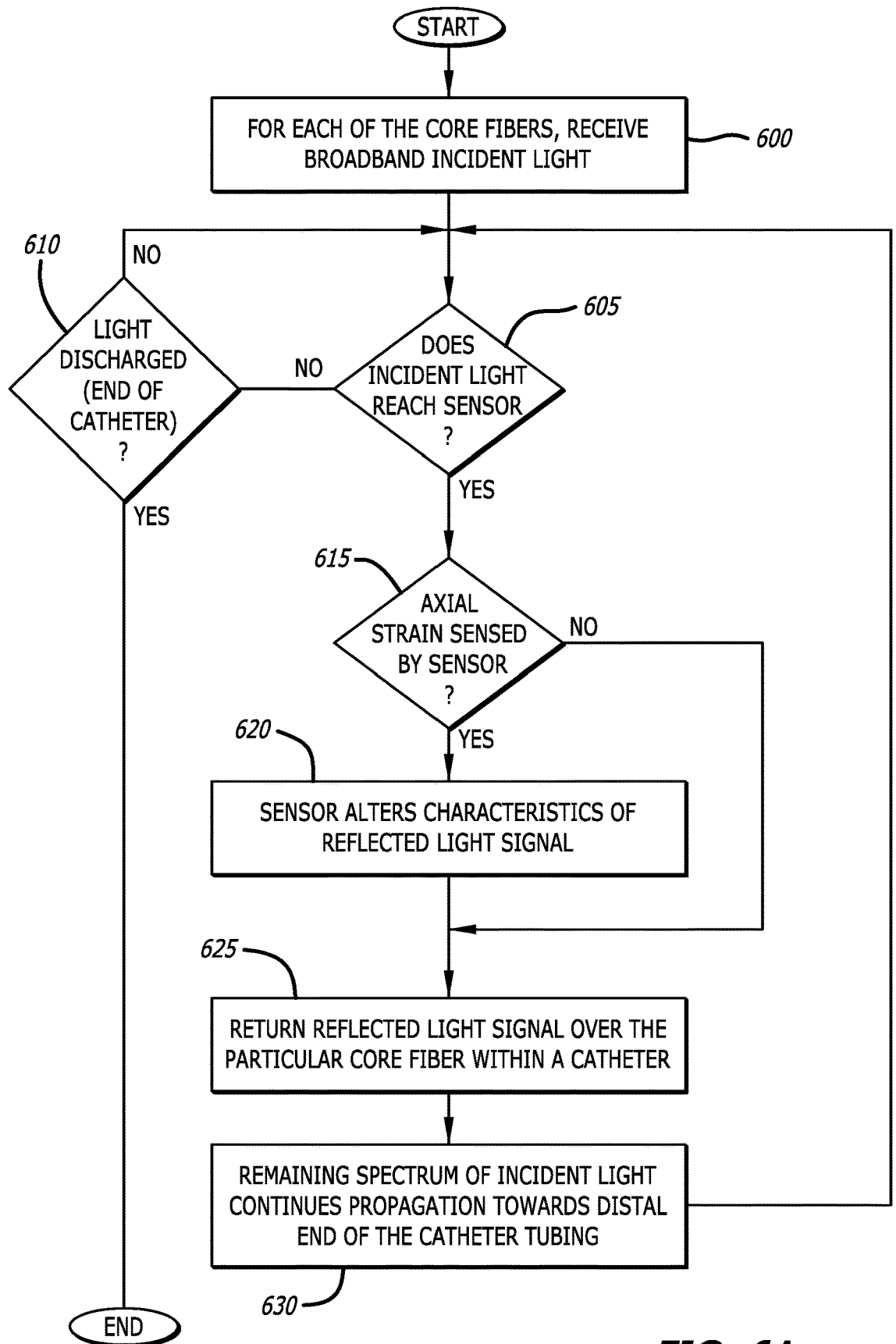
FIGS. 6A-6B is a flowchart of the method of operations conducted by the medical instrument monitoring system of FIG. 1 to achieve optic 3-D shape sensing.
Figure 6B:
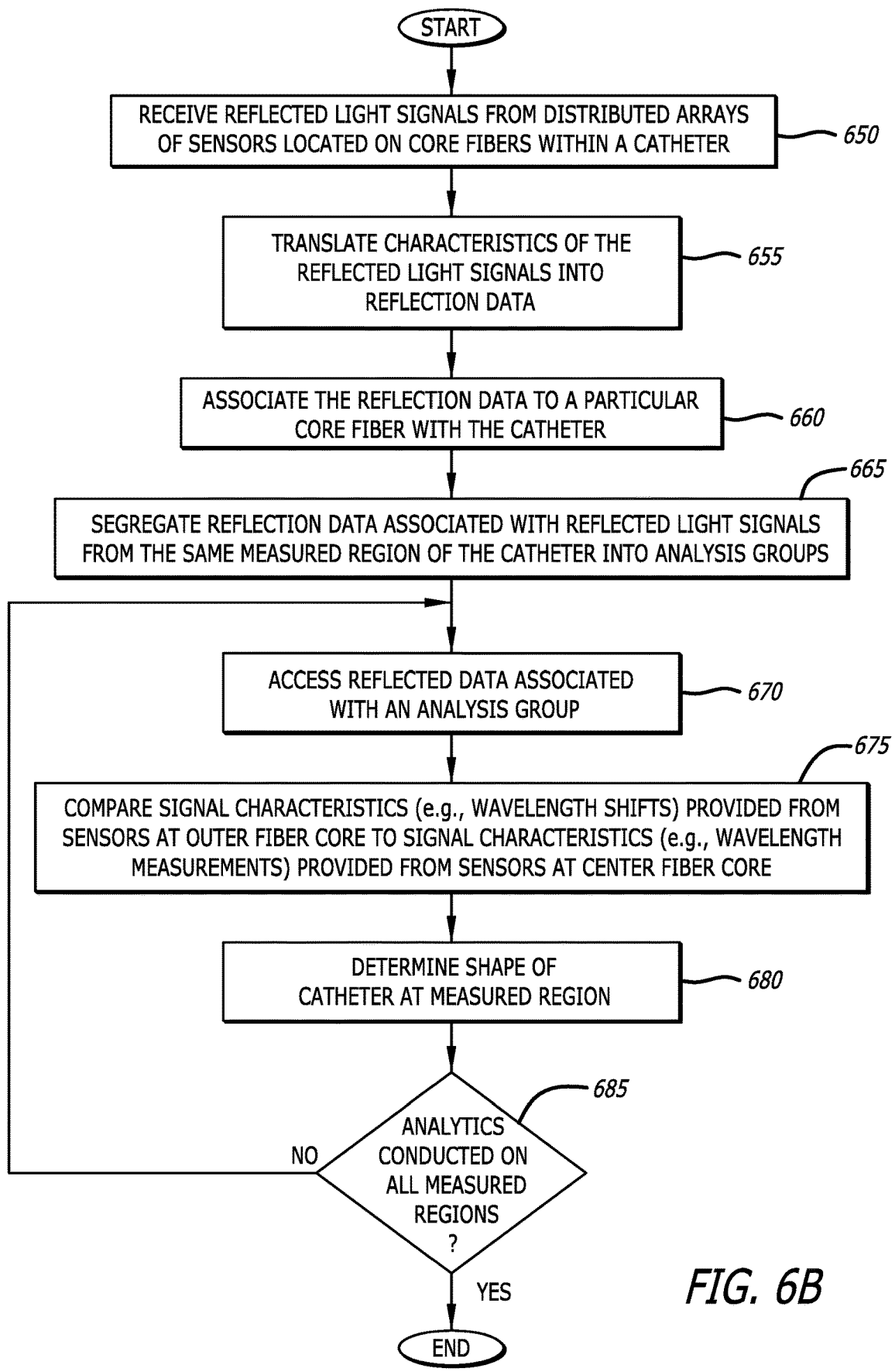

Referring now to FIG. 6A-6B, flowcharts of the method of operations conducted by components of the medical instrument monitoring system of FIG. 1 to achieve optic 3-D shape sensing is shown. Herein, the catheter includes at least one septum spanning across a diameter of the tubing wall and continuing longitudinally to subdivide the tubing wall. The medial portion of the septum is fabricated with a first micro-lumen, where the first micro-lumen is coaxial with the central axis of the catheter tubing. The first micro-lumen is configured to retain a center core fiber. Two or more micro-lumen, other than the first micro-lumen, are positioned at different locations circumferentially spaced along the wall of the catheter tubing. For example, two or more of the second plurality of micro-lumens may be positioned at different quadrants along the circumference of the catheter wall.

Furthermore, each core fiber includes a plurality of sensors spatially distributed along its length between at least the proximal and distal ends of the catheter tubing. This array of sensors are distributed to position sensors at different regions of the core fiber to enable distributed measurements of strain throughout the entire length or a selected portion of the catheter tubing. These distributed measurements may be conveyed through reflected light of different spectral widths (e.g., specific wavelength or specific wavelength ranges) that undergoes certain wavelength shifts based on the type and degree of strain.

According to one embodiment of the disclosure, as shown in FIG. 6A, for each core fiber, broadband incident light is supplied to propagate through a particular core fiber (block 600). Unless discharged, upon the incident light reaching a sensor of a distributed array of sensors measuring strain on a particular core fiber, light of a prescribed spectral width associated with the first sensor is to be reflected back to an optical receiver within a console (blocks 605-610). Herein, the sensor alters characteristics of the reflected light signal to identify the type and degree of strain on the particular core fiber as measured by the first sensor (blocks 615-620). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the catheter tubing (blocks 625-630). The remaining spectrum of the incident light may encounters other sensors of the distributed array of sensors, where each of these sensors would operate as set forth in blocks 605-630 until the last sensor of the distributed array of sensors returns the reflected light signal associated with its assigned spectral width and the remaining spectrum is discharged as illumination.

Referring now to FIG. 6B, during operation, multiple reflected light signals are returned to the console from each of the plurality of core fibers residing within the corresponding plurality of micro-lumens formed within the catheter. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 650-655). The reflection data classification logic is configured to identify which core fibers pertain to which reflection data and segregate reflection data provided from reflected light signals pertaining to a particular measurement region (or similar spectral width) into analysis groups (block 660-665).

Each analysis group of reflection data is provided to shape sensing logic for analytics (block 670). Herein, the shape sensing logic compares wavelength shifts at each outer core fiber with the wavelength shift at the center core fiber positioned along central axis and operating as a neutral axis of bending (block 675). From this analytics, on all analytic groups (e.g., reflected light signals from sensors in all or most of the core fibers), the shape sensing logic may determine the shape the core fibers have taken in three-dimensional space, from which the shape sensing logic can determine the current physical state of the catheter in three-dimension space (blocks 680-685).

Embodiments of the invention may be embodied in other specific forms without departing from the spirit of the present disclosure. The described embodiments are to be considered in all respects only as illustrative, not restrictive. For example, in lieu of placing the micro-lumens within the wall of the integrated tubing, longitudinal beads may be formed along the interior surfaces of the wall occupying a portion of a lumen or the micro-lumens may be formed along an outer surface of the integrated tubing as described above. The scope of the embodiments is, therefore, indicated by the appended claims rather than by the foregoing description. All changes that come within the meaning and range of equivalency of the claims are to be embraced within their scope.

What is claimed is:

1. A catheter, comprising:
    an elongated tubing including an opening at a distal end of the tubing, the tubing being formed by an axial wall defining a lumen extending between a proximal end of the tubing to the distal end of the tubing;
    a septum positioned across the opening of the tubing;
    a first micro-lumen formed in the septum;
    a plurality of micro-lumens formed along a circumference of the wall forming the tubing;
    a first core fiber residing within the first micro-lumen; and
    a plurality of core fibers each residing within a different micro-lumen of the plurality of micro-lumens, wherein at least one of the plurality of micro-lumens is sized with a diameter to fixedly retain one of the plurality of core fibers, such that there is no spacing between a lateral surface of the one of the plurality of core fibers and an interior wall surface of the at least one of the plurality of micro-lumens,
    wherein:
        a plurality of sensors are distributed along a longitudinal length of both the first core fiber and each of the plurality of core fibers and each sensor of the plurality of sensors being configured to (i) reflect a light signal of a different spectral width based on received incident light and (ii) change a characteristic of the reflected light signal for use in determining a physical state of the catheter,
        a characteristic of the reflected light signal for the plurality of core fibers is compared with a characteristic of the reflected light signal for the first core fiber to determine the physical state of the catheter, and
        the characteristic of the reflected light signal is configured such that the physical state of the catheter is determined utilizing machine-learning techniques that include accessing a data store with pre-stored data, including image data, pertaining to different regions of the catheter in which the plurality of core fibers experienced a similar characteristic of the reflected light signal.

2. The catheter as defined in claim 1, wherein the first micro-lumen is formed within the septum along an axis central to a cross-section of the tubing.

3. The catheter as defined in claim 1, wherein the plurality of micro-lumens are formed between an inner surface of the wall and an outer surface of the wall forming the tubing, each of the plurality of micro-lumens extending from the distal end of the tubing to a proximal portion of the tubing.

4. The catheter as defined in claim 1, wherein each of the plurality of sensors constitutes a reflective grating positioned at a different region of a particular core fiber of the plurality of core fibers.

5. The catheter as defined in claim 1, wherein the change in the characteristic of the reflected light signal includes a shift in wavelength applied to the reflected light signal to identify at least a type of strain.

6. The catheter as defined in claim 5, wherein the type of strain is a compression strain or a tension strain.

7. The catheter as defined in claim 1, wherein the first micro-lumen formed along an axis central to a cross-section of the tubing and two or more of the plurality of micro-lumens are formed within the wall of the tubing radiating from the central axis.

8. The catheter as defined in claim 1, wherein (i) a second core fiber of the plurality of core fibers residing within a second micro-lumen of the plurality of micro-lumens is oriented in a first radial direction from the first micro-lumen and positioned within a first arc segment of the wall, (ii) a third core fiber of the plurality of core fibers residing within a third micro-lumen of the plurality of micro-lumens is oriented in a second radial direction from the first micro-lumen and positioned within a second arc segment of the wall separate from the first arc segment, and (iii) a fourth core fiber of the plurality of core fibers residing within a fourth micro-lumen of the plurality of micro-lumens is oriented in a third radial direction from the first micro-lumen and positioned within a third arc segment of the wall separate from both the first arc segment and the second arc segment.

9. The catheter as defined in claim 1, further comprising the plurality of core fibers including the first core fiber residing within the first micro-lumen formed along a central axis of the tubing and a second plurality of core fibers each residing within a micro-lumen radially distributed from the central axis with each of the second plurality of core fibers being positioned within a second micro-lumen of the plurality of micro-lumens.

10. The catheter as defined in claim 9, wherein the second plurality of core fibers includes a second core fiber residing within a second micro-lumen formed coplanar to the first micro-lumen, a third core fiber residing within a third micro-lumen formed radially from the first micro-lumen forming an obtuse angle between the second micro-lumen and the third micro-lumen, and a fourth core fiber residing within a fourth micro-lumen formed radially from the first micro-lumen forming a first obtuse angle between the second micro-lumen and the fourth micro-lumen and a second obtuse angle between the third micro-lumen and the fourth micro-lumen.

11. The catheter as defined in claim 1, wherein at least a second micro-lumen of the plurality of micro-lumens is formed as a longitudinal bead being a conduit formed on or attached to an outer surface of the axial wall forming the tubing.

12. The catheter as defined in claim 1, wherein each of the plurality of micro-lumens are sized with a diameter to fixedly retain the plurality of core fibers.

13. A catheter, comprising:
an elongated tubing including a distal end, the tubing being formed by an axial wall defining a lumen extending between a proximal end of the tubing to the distal end of the tubing;
a septum positioned across the distal end of the tubing;
a first micro-lumen formed along an axis central to a cross-section of the distal end of the tubing;
one or more micro-lumens formed along a circumference of the wall forming the tubing;
a first core fiber residing within the first micro-lumen; and
one or more core fibers each residing within a different micro-lumen of the one or more micro-lumens,
wherein at least one of the one or more micro-lumens is sized with a diameter to fixedly retain one of the one or more core fibers, such that there is no spacing between a lateral surface of the one of the one or more core fibers and an interior wall surface of the at least one of the one or more micro-lumens, and
wherein:
a plurality of sensors are distributed along a longitudinal length of both the first core fiber and each of the one or more core fibers and each sensor of the plurality of sensors being configured to (i) reflect a light signal of a different spectral width based on received incident light and (ii) change a characteristic of the reflected light signal for use in determining a physical state of the catheter,
a characteristic of the reflected light signal for the one or more core fibers is compared with a characteristic of the reflected light signal for the first core fiber to determine the physical state of the catheter, and
the characteristic of the reflected light signal is configured such that the physical state of the catheter is determined utilizing machine-learning techniques that include accessing a data store with pre-stored data, including image data, pertaining to different regions of the catheter in which the one or more core fibers experienced a similar characteristic of the reflected light signal.

14. The catheter of claim 13, wherein the distal end of the tubing includes an opening.

15. The catheter as defined in claim 13, wherein the first micro-lumen is formed within the septum between edges of the distal end of the tubing.

16. The catheter as defined in claim 15, wherein the septum extends along a diameter of the cross-section of the distal end of the tubing.

17. The catheter as defined in claim 13, wherein the one or more micro-lumens are formed between an inner surface of the wall and an outer surface of the wall forming the tubing, each of the one or more micro-lumens extending from the distal end of the tubing to a proximal portion of the tubing.

18. The catheter as defined in claim 13, wherein each of the plurality of sensors constitutes a reflective grating positioned at a different region of a particular core fiber of the one or more core fibers.

19. The catheter as defined in claim 13, wherein the change in the characteristic of the reflected light signal includes a shift in wavelength applied to the reflected light signal to identify at least a type of strain.

20. The catheter as defined in claim 19, wherein the type of strain being a compression or a tension.

21. The catheter as defined in claim 13, wherein a plurality of micro-lumens of the one or more micro-lumens are formed within the wall of the tubing radiating from the central axis.

22. The catheter as defined in claim 13, wherein (i) a second core fiber of the one or more core fibers residing within a second micro-lumen of the one or more micro-lumens is oriented in a first radial direction from the first micro-lumen and positioned within a first arc segment of the wall, (ii) a third core fiber of the one or more core fibers residing within a third micro-lumen of the one or more micro-lumens is oriented in a second radial direction from the first micro-lumen and positioned within a second arc segment of the wall separate from the first arc segment, and (iii) a fourth core fiber of the one or more core fibers residing within a fourth micro-lumen of the one or more micro-lumens is oriented in a third radial direction from the first micro-lumen and positioned within a third arc segment of the wall separate from both the first arc segment and the second arc segment.

23. The catheter as defined in claim 13, further comprising the one or more core fibers including the first core fiber residing within the first micro-lumen formed along the central axis of the tubing and the one or more core fibers each residing within a micro-lumen of the one or more micro-lumens radially distributed from the central axis with each of the one or more core fibers being positioned within a different micro-lumen of the one or more micro-lumens.

24. The catheter as defined in claim 13, wherein the one or more core fibers includes a second core fiber residing within a second micro-lumen formed coplanar to the first micro-lumen, a third core fiber residing within a third micro-lumen formed radially from the first micro-lumen forming an obtuse angle between the second micro-lumen and the third micro-lumen, and a fourth core fiber residing within a fourth micro-lumen formed radially from the first micro-lumen forming a first obtuse angle between the second micro-lumen and the fourth micro-lumen and a second obtuse angle between the third micro-lumen and the fourth micro-lumen.

25. The catheter as defined in claim 13, wherein at least a second micro-lumen of the one or more micro-lumens is formed as longitudinal bead being a conduit formed on or attached to an outer surface or an inner surface of the axial wall forming the tubing.

26. The catheter as defined in claim 13, wherein each of the one or more micro-lumens are sized with a diameter to fixedly retain the one or more core fibers.

* * * * *